United States Patent
Duncan

(10) Patent No.: US 8,932,522 B2
(45) Date of Patent: Jan. 13, 2015

(54) REVOLUTIONARY TOOTHBRUSH CLEANER

(76) Inventor: Opal Marie Duncan, Winnipeg (CA)

( * ) Notice: Subject to any disclaimer, the term of this patent is extended or adjusted under 35 U.S.C. 154(b) by 712 days.

(21) Appl. No.: 13/005,324

(22) Filed: Jan. 12, 2011

(65) Prior Publication Data

US 2011/0155172 A1   Jun. 30, 2011

Related U.S. Application Data

(63) Continuation-in-part of application No. 11/294,804, filed on Dec. 7, 2005, now abandoned.

(51) Int. Cl.
*A61L 2/00* (2006.01)
(52) U.S. Cl.
USPC .......................... 422/28; 422/300; 206/209.1
(58) Field of Classification Search
CPC ............. A61L 2/26; A61L 2/18; A46B 17/06
USPC .................................. 422/28, 300; 206/209.1
See application file for complete search history.

(56) References Cited

U.S. PATENT DOCUMENTS 4,995,509 A * 2/1991 Kornfeind .................. 206/209.1
6,045,280 A * 4/2000 Nadel et al. .................... 401/122

* cited by examiner

*Primary Examiner* — Kevin Joyner
(74) *Attorney, Agent, or Firm* — Kyle R. Satterthwaite; Ryan W. Dupuis; Ade & Company Inc.

(57) ABSTRACT

An apparatus for cleaning a toothbrush comprises a hollow container having an interior with an upper section and a lower section. The upper section is open for allowing insertion and withdrawal of a toothbrush along an axis and the lower section defines a reservoir for storing a cleaning fluid. A plurality of fins are mounted to the container and arranged about the axis to project inward toward the axis at a distance above a bottom of the reservoir. The distal ends of the fins are spaced for deflecting bristles of the toothbrush during passage of the toothbrush along the axis past the distal ends of the fins from one side of the plurality of fins to another side of the plurality of fins. An additional set of fins is provided for drying excess cleaning fluid from the brush. The fins are removable from the container for thorough cleaning or replacement.

7 Claims, 4 Drawing Sheets

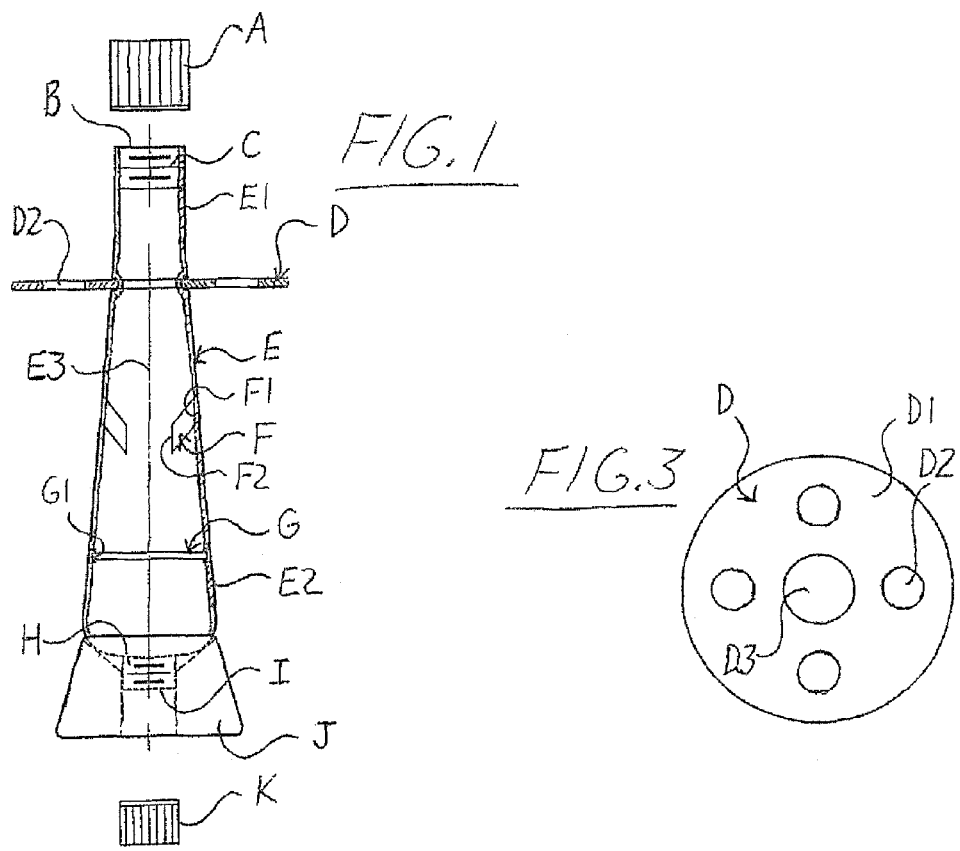
FIG. 1
FIG. 3
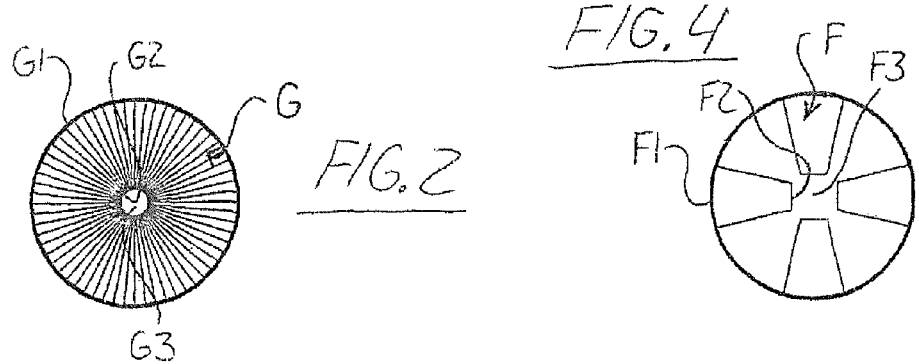
FIG. 2
FIG. 4

US 8,932,522 B2

REVOLUTIONARY TOOTHBRUSH CLEANER

CROSS REFERENCE TO RELATED APPLICATIONS

This application is a continuation in part of U.S. application Ser. No. 11/294,804, filed Dec. 7, 2005.

TECHNICAL FIELD

The present invention relates to a toothbrush cleaner for cleaning toothbrushes.

BACKGROUND OF THE INVENTION

The inventions intention is to promote healthy teeth and gums, and also to kill bacteria before they get into your mouth. Often toothbrushes are stored uncovered on counter tops or in sanitized holders where they are exposed to germs and contaminants in the air. This toothbrush holder is designed to sanitize the toothbrush by immersing the bristles in a sanitizing liquid. To store the toothbrush/toothbrushes, the bristles should be facing down. When the bristle portion of the toothbrush is submerged into the liquid, you can move your toothbrush in an upward and downward motion, to remove build-up and bacteria. Bacteria are everywhere floating around on our toothbrushes. By using this solution you can kill 99.9% of bacteria on your toothbrush, by using this solution and the toothbrush container. You can use it everywhere. You can take this container in your purse, suitcase/briefcase, to work, etc. It is small and compact, so don't leave your home without it.

SUMMARY OF THE INVENTION

According to a first aspect of the invention there is provided an apparatus for cleaning a toothbrush, the apparatus comprising:

a hollow container having an interior with an upper section and a lower section, the upper section being open for allowing insertion and withdrawal of a toothbrush along an axis and the lower section defining a reservoir for storing a cleaning fluid; and at least one cleaning fin provided on the container and projecting inward into the interior thereof toward the axis at a distance above a bottom of the reservoir;

wherein the at least one fin has a connection end connected to the container and a cleaning end opposite the connection end and nearest the axis, the cleaning end being disposed in a plane generally normal to the axis for positioning of the cleaning end between the bristles of the toothbrush during passage of the head of the toothbrush along the axis from one side of the at least one cleaning fin to another side of the at least one cleaning fin.

Preferably there is provided an upper cap selectively engagable to the upper section of the container for closing thereof.

Preferably there is provided a lower cap engaged to the lower section to close the reservoir at the bottom thereof, the lower cap being selectively removable to drain the cleaning fluid.

Preferably there is provided a base with which the lower section of the container is engagable to support the container atop the base.

Preferably the at least one cleaning fin comprises a plurality of cleaning fins arranged about the axis.

Preferably there is provided at least one additional fin provided on the container to project inward into the interior thereof toward the axis, the at least one additional fin being spaced above the at least one cleaning fin.

Preferably the at least one additional fin comprises a plurality of additional fins arranged about the axis.

According to another aspect of the invention there is provided a method of cleaning a toothbrush, the method comprising:

(a) obtaining a toothbrush cleaning apparatus comprising:
   a hollow container having an interior with an upper section and a lower section, the upper section being open for allowing insertion and withdrawal of the toothbrush along an axis of the container and the lower section defining a reservoir containing a cleaning liquid;
   at least one cleaning fin provided on the container at a distance above a bottom of the reservoir and projecting inwardly in the interior of the container toward, without reaching, the axis; and
   at least one additional fin spaced above the at least one cleaning fin and projecting inwardly in the interior of the container toward, without reaching, the axis;

(b) submerging bristles of the toothbrush in the cleaning liquid in the reservoir;

(c) with bristles on a head of the toothbrush positioned against the at least one cleaning fin, cleaning the bristles by moving the toothbrush in an upward and downward motion along the axis to position the cleaning end of the cleaning fin between the bristles as the bristles move from one side of the cleaning fin to another side thereof during passage of the head of the toothbrush along the axis; and (d) drying the bristles by pulling the bristles past the distal end of the additional fin to cause deflection of the bristles and shake off excess cleaning liquid therefrom.

Preferably the at least one cleaning fin comprises a plurality of cleaning fins having lengths insufficient to reach the axis and leaving an opening between the cleaning fins at said axis.

Preferably the at least one additional fin comprises a plurality of additional fins spaced above the cleaning fins.

Preferably there is an additional step (e) that includes removing the at least one cleaning fin that was used in step (c) from the interior of the container.

Step (e) may comprise cleaning the at least one cleaning fin that was used in step (c) after removal thereof from the interior of the container, and placing the at least one cleaning fin used in step (c) back into the interior of the container for re-use.

Alternatively, step (e) may comprise replacing the at least one cleaning fin that was used in step (c) with at least one new cleaning fin.

The method may include at least one repetition of steps (c) and (d) before performing step (e).

According to yet another aspect of the invention, there is provided a toothbrush cleaner comprising:

a hollow container with a hollow interior space having an upper section and a lower section, the upper section being open for allowing insertion and withdrawal of a toothbrush along an axis and the lower section defining a reservoir for storing a cleaning fluid; and a removable cleaning structure disposed in the hollow interior space and selectively removable from the container, the removable structure including at least one cleaning fin inwardly toward the axis at a distance above a bottom of the reservoir, a cleaning end of the cleaning fin being positioned nearest the axis in a plane generally normal thereto in order to position the cleaning end between the bristles of the toothbrush during passage of the head of the toothbrush along the axis from one side of the at least one cleaning fin to another side of the at least one cleaning fin.

Preferably the removable cleaning structure comprises a tubular insert dimensioned to slide into and out of the hollow interior space at the upper section thereof, the at least one cleaning fin extending inward from a wall of the tubular insert.

Preferably the container defines a ledge projecting inward from a peripheral wall of the interior space to define a seat on which the tubular insert is received.

Preferably there is provided a cap engagable onto the container and arranged to maintain a position of the removable cleaning structure in the hollow interior space when engaged on the container, the cap having an opening through which the hollow interior space is accessible.

Preferably there is provided at least one additional fin project inwardly within the hollow interior space toward the axis, the at least one additional fin being spaced above the at least one cleaning fin and also being selectively removable from the container.

The cap is preferably arranged to maintain a position of the removable cleaning structure and additional fin in the hollow interior space when engaged on the container.

Preferably the at least one additional fin is on a removable drying structure arranged to sit atop the removable cleaning structure.

Preferably the cap is arranged to fit over the removable drying structure to maintain the removable drying structure in a position between the removable cleaning structure and the cap.

Preferably the container comprises multiple hollow interior spaces, each having at least one respective removable cleaning structure.

BRIEF DESCRIPTION OF THE DRAWINGS

The invention is best understood with the following detailed description, when read with the accompanying drawings. Included in the drawing are the following figures:

FIG. 1 is an elevational view of a toothbrush cleaner according to an embodiment of the present invention with a container and a toothbrush holder of the toothbrush cleaner cut away.

FIG. 2 is a plan view of lower fins of the toothbrush cleaner shown in FIG. 1 that clean the toothbrush bristles.

FIG. 3 is a plan view of a toothbrush holder of the toothbrush cleaner shown in FIG. 1 where you can store your toothbrush, when not cleaning.

FIG. 4 is a plan view of upper fins of the toothbrush cleaner shown in FIG. 1 that will take excess liquid off your toothbrush

DETAILED DESCRIPTION

Figure 5:
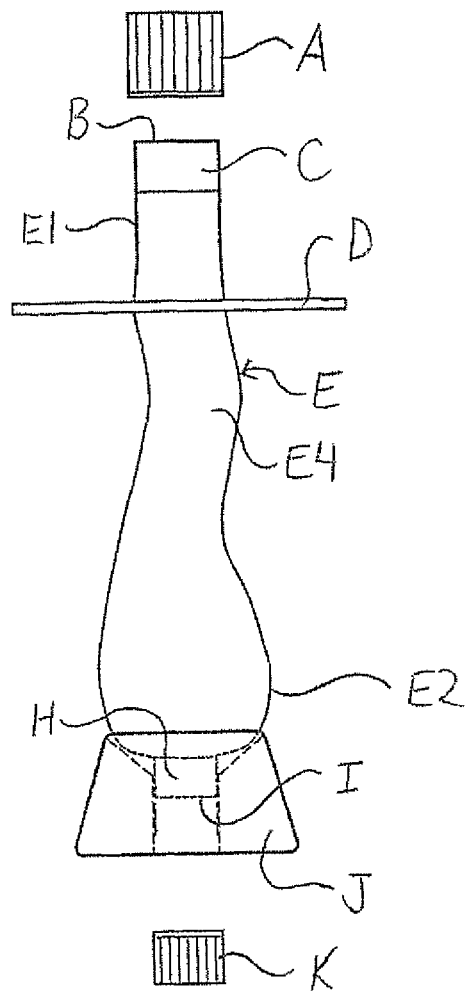
FIG. 5 is an elevational view of a toothbrush cleaner according to an alternate embodiment.

As shown in FIG. 1, top lid A, and top ridge C are locked together, to prevent spills. The top lid A and top ridge C interlock together to prevent spilling and provide safety in the form of a child lock. The top opening B allows you to pour liquid or antibacterial solution into the container and submerge toothbrush bristles into the solution. The toothbrush holder D can hold up to four toothbrushes for storage when they are not being sterilized. The toothbrush holder D is portable and can be removed from the container for traveling purposes. The cleaning container E contains two different sets of working fins, upper fins F and lower fins G against which the bristles of the toothbrush are movable in an upward and downward motion. When the toothbrush bristles are submerged into the solution in the bottom of the container, the toothbrush handle is pulled manually in an upward and downward motion. The upper fins F act to dry excess liquid. The lower fins G work together with the solution to clean, kill bacteria, and remove food and build-up from your toothbrush bristles. The container has two openings, the top opening B and a bottom opening I. Bottom opening I is used to drain the solution from the container. A stand/base J is free standing and arranged to hold to container and keep it sturdy and firm. A bottom lid K and a bottom ridge H work together to prevent spills and provide a child safety lock similar to that provided by top lid A and top ridge C.

FIG. 2 shows the lower fins, or cleaning fins, G of FIG. 1 in a plan view. The cleaning fins have several different fins with space in the middle, to get into your toothbrush bristles. The fins purpose is to clean food and build-up from the toothbrush bristles. The solution kills bacteria from the toothbrush bristles. After pouring the sterilizing liquid or mouthwash solution into the container, the toothbrush bristles are placed into the solution. The toothbrush handle is moved in an upward and downward motion to move the bristles against the lower fins G, to remove food, build-up, and bacteria.

FIG. 3 shows a plane view of the toothbrush holder D of FIG. 1, which has storage capability for four toothbrushes. It is easy to remove from the container, and is portable for traveling purposes. The holder is the resting place for toothbrushes, before or after cleaning of the toothbrush bristles.

FIG. 4 shows the upper fins F of FIG. 1. The purpose of the upper fins is to dry excess liquid from the toothbrush bristles. There are four separate upper fins that dry excess liquids and a space in the middle to clean toothbrush bristles. It has four fins, that are equally spaced out inside. You submerge your toothbrush into the center to dry excess liquid.

As shown in FIG. 1, the hollow container E has a hollow interior with an upper section E1 and a lower section E2. A toothbrush having a handle and a bristle equipped head (not shown) can be inserted into and withdrawn from the container's interior along a central axis E3 thereof through the top opening B at the top of the upper section E1. The lower section E2 forms a reservoir for storing the fluid for cleaning the toothbrush and killing bacteria thereon. The lower cleaning fins G provided on the container E project inward into the interior thereof toward the axis E3 at a distance above a bottom of the reservoir defined by the bottom opening I when closed by the bottom lid K.

As shown by FIGS. 1 and 2, the lower cleaning fins G are each connected at one end G1 to the container and each project inward to an opposite end G2 nearest the axis E3. The container E is of round cross-section and the fins are all of the same length, which is not sufficient to reach the axis E3, thereby forming a round opening G3 at the center of the fins surrounding the axis E3 of the container. The cleaning ends G2 of the fins G opposite the connection ends G1 and nearest the axis E3 are disposed in a plane generally normal to the axis E3 as shown in FIG. 1 by the horizontal positioning of the fins G and the vertical orientation of the container axis E3. As illustrated by FIG. 1, the fins G are planar and thus all lie in this common horizontal plane normal to the container axis, and, as illustrated by FIG. 2, each of the fins G is tapered in this plane to narrow in width from its connection end G1 to its cleaning end G2. A person of skill in the art will appreciate that the cleaning ends of the lower fins need not be perfectly normal to the axis along which the brush head moves, but should extend more across than along the brush head being moved past them.

The toothbrush holder D of FIGS. 1 and 3 includes a disc shaped body D1 having a plurality of apertures D2 therethrough spaced around a central opening D3 through the body D1. As illustrated by FIG. 1, the central opening D3 is sized to fit over the top end of the container E to slide the body D1 downward along the container to snap into a groove in the exterior of the upper section E1 defining a ridge or ledge on which the toothbrush holder can sit. At each aperture D2, the toothbrush holder D can store a toothbrush in a manner already well-known to those of skill in the art, by supporting the head of the toothbrush atop the disc shaped body D1 after passing the toothbrush handle through the aperture. To achieve this effect, it is well-known that the bristle equipped head of the toothbrush must be larger than the aperture D2. Thus, comparing FIGS. 1 and 2, it will be appreciated that the opening G3 enclosed by the cleaning ends G2 of the lower fins G is smaller than the apertures D2 in the toothbrush holder D. Therefore, a person of skill in the art will appreciate that rows of the resilient bristles extending across the toothbrush head will deflect to pass through the opening G3 and the fins G project between rows of bristles to their cleaning ends G2 during passage of the toothbrush head along the axis E3 from one side of the cleaning lower fins G to an opposite side thereof.

As shown in FIG. 4, the upper fins F are similar to the lower fins G in that they have connection ends F1 connected to the container E and distal ends F2 opposite this connection. From FIG. 4, it can be seen that the upper fins F are different in that there are only four of them, they are angularly spaced apart from one another about the axis E3 and the opening F3 between their distal ends F2 is larger. From FIG. 1, it can be seen that the upper fins depend somewhat downward in their projection toward the axis E3 and thus are not horizontally extending like the lower fins G. As shown in FIG. 1, the distal ends F2 lie at the same height as one another, but the upper fins F are significantly thicker than the lower fins G. As will be appreciated from the figures by those of skill in the art, the upper fins F2 provide edges against past which the bristles can be pulled upwardly when withdrawing the toothbrush from the container E to cause deflection and resilient return of the bristles to shake off excess fluid.

As will be appreciated by those of skill in the art, as little as one wider lower fin G projecting from only one side of the axis E3 could also project between rows of bristles during movement past its cleaning edge opposite the connection to the container, but a person of skill in the art will appreciate that the surrounding arrangement as shown in FIG. 2 with fins arranged entirely around a central axis provides projection into the bristles from many directions to provide a thorough cleaning action.

Figure 6:
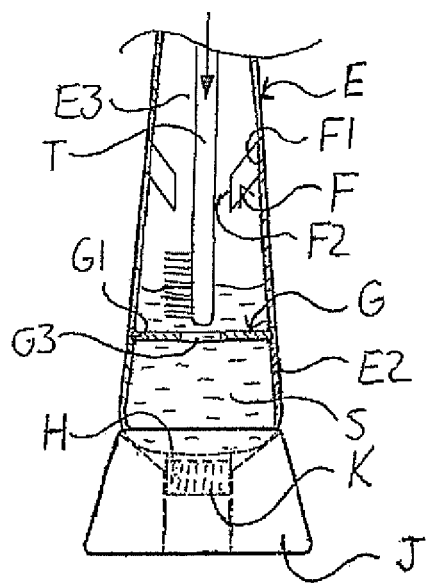
FIG. 6 features partial elevational views of the toothbrush cleaner of FIG. 1 with the container cut away to illustrate use of the toothbrush cleaner to clean and dry a toothbrush.
Figure 6:
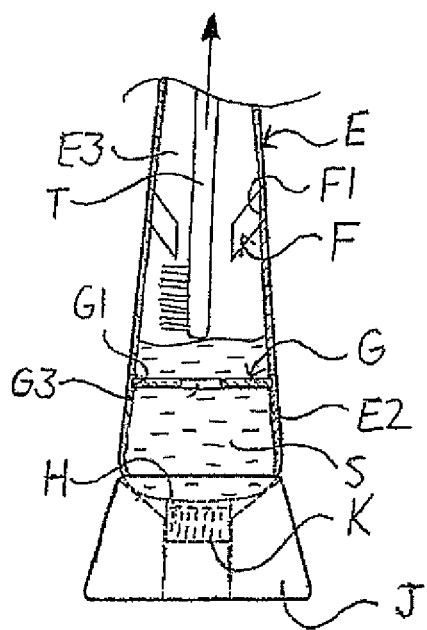

FIG. 6 illustrates cleaning of a toothbrush with the present invention. With reference to Part A of the figure, a liquid cleaning solution S is poured into the reservoir to fill the reservoir to a level L above the cleaning fins G, and a toothbrush T is lowered into the container to submerge the bristles on the head of the toothbrush in the liquid. As described above, while bristles of the toothbrush are submerged, the toothbrush handle is pulled manually in an upward and downward motion through the opening G3 between the cleaning fins G to clean the bristles of the brush. To provide this cleaning action, the cleaning fins G are rigid and accordingly maintain the cleaning ends G2 of the fins G at fixed stationary positions relative to their connections ends at the container wall so as to work between the bristles as they pass through the opening G3. The opening G3 between the cleaning fins G is larger than a cross-section of the head portion of the toothbrush body in the plane along which the bristles project so that the head of the toothbrush can fit through the opening G3. Alternatively, the cleaning fins may have a small degree of flexibility to them to better accommodate varying toothbrush sizes, while maintaining enough rigidity to penetrate between the bristles deflecting against them. As is also shown in FIG. 1, the cleaning fins are nearer to the bottom of the reservoir than the open top end of the container.

As described above and illustrated in Part B of FIG. 6, drying of the brush bristles after the cleaning of the brush by the lower fins is effected by pulling the bristles upward past the edges at the distal ends of the upper fins to cause deflection of the resilient bristles to shake off excess cleaning fluid therefrom. Like the lower fins, the upper finds F may be rigid and stationary in their positions mounted on the container wall, and open space left between the distal ends F2 of the upper drying fins F is likewise larger than the cross-section of the brush's head portion to accommodate passage of the toothbrush head through the open space. Again, these fins may have some flexibility to them in other embodiments, while still being rigid enough to form a resistant obstruction to the bristles so that the bristle ends deflect to shake off excess cleaning solution.

Figure 8:
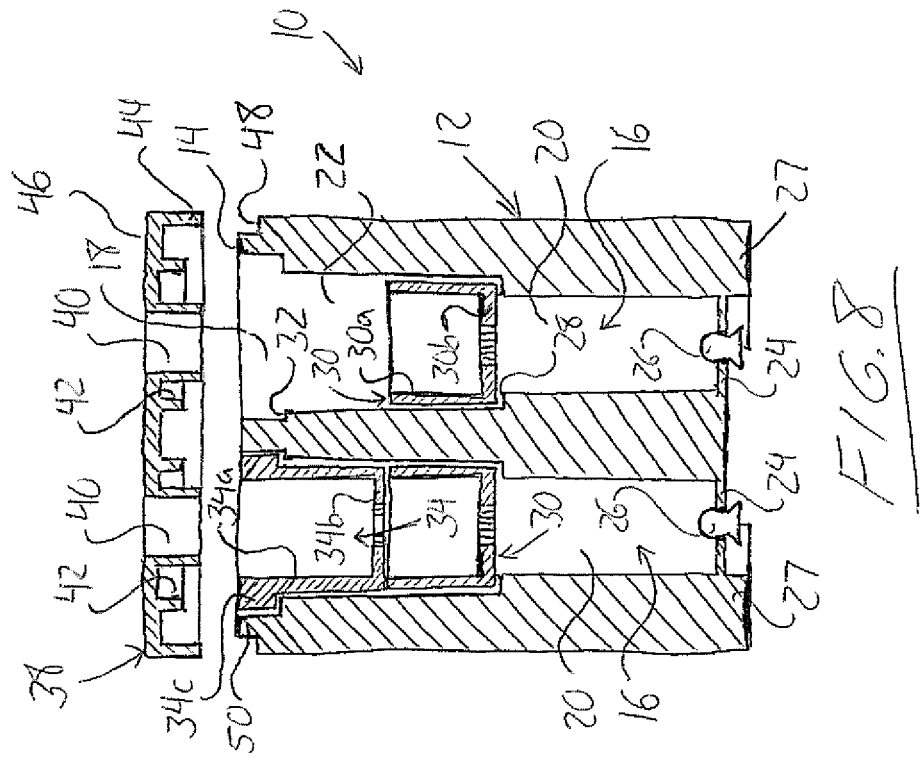
FIG. 8 is a cross-sectional view of the toothbrush cleaning of FIG. 7 as taken along line A-A thereof.
Figure 7:
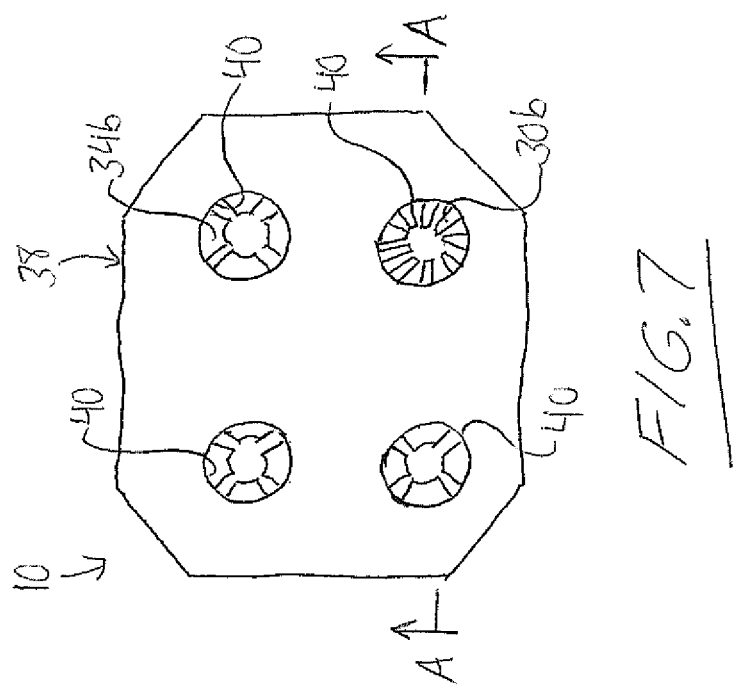
FIG. 7 is an overhead plan view of a second embodiment toothbrush cleaner arranged to accommodate storage and cleaning of up to four toothbrushes.

FIGS. 7 and 8 show a second embodiment toothbrush cleaner 10 that is operable to store and clean multiple toothbrushes. A container body 12 features four hollow interior cavities each having an elongate shape of circular cross-section and extending into the container body 12 from a top end 14 thereof. Each cavity 16 is divided into three cylindrical sections: a top section 18 of largest diameter, a bottom section 20 of smallest diameter, and a middle section 22 of a medium diameter between those of the other two sections. The lower end of the cavity has an end wall 24 to close off the bottom end of the cavity and thus form the reservoir for filling with a cleaning solution. Instead of a threaded coupling with a lower cap, a resilient plug 26 is releasably engaged in a central opening in the bottom wall 24 of the cavity 16 to close the bottom of the reservoir. When the reservoir is to be emptied, the plug 26 is manually withdrawn from the bottom wall 24 to release the cleaning fluid from the reservoir. Feet 27 at corners of the container elevate the cavity bottom off the surface on which the container stands, thus leaving room to accommodate the plug between the cavity bottom and the container-supporting surface.

The step-wise decrease in diameter of the hollow cavity space 16 in a downward direction therealong creates two annular ledges each jutting inward from the cylindrical inner wall surface of the cavity section above it. The lower ledge 28 between the bottom and middle sections 20, 22 forms a lower seat on which a cleaning fin insert 30 is seated, while the upper ledge 32 between the top and middle sections 18, 22 forms an upper seat on from which a drying fin insert 34 is hung. The cleaning fin insert 30 is a unitary body having a cylindrical sleeve or tubular portion 30a, at the bottom end of which cleaning fins 30b like those of the other embodiments project radially inward from the sleeve 30a toward a central axis thereof. The cleaning fins 30b do not reach the axis around which the cylindrical sleeve closes, and therefore leave a generally circular opening between the fins at the axis to accommodate passage of a toothbrush head through the opening to clean the toothbrush bristles against the inner cleaning ends of the fins 30b. The bottom end face of the cylindrical sleeve portion 30a sits atop the lower ledge 28 of the cavity wall. The drying fin insert 34 likewise has a cylindrical tubular or sleeve portion 34a and has drying fins 34b projecting inwardly from the sleeve wall at the bottom end thereof by a distance leaving an open space between the fins at the central axis of the sleeve. Unlike the upper fins of the other embodiments, these drying fins 34b are planar like the cleaning fins, giving the drying fin insert 34 a flat planar bottom so that the annular bottom face of the drying insert's sleeve portion 34a can sit flat atop the annular top face of the cleaning insert's sleeve portion 30a. The drying fin insert 34 also features an annular flange 34c projecting radially outward at the upper end of the sleeve portion 34a to present an annular shoulder for seating on the upper ledge 32 of the cavity wall in the upper cavity section 18.

The left of the two container cavities visible in FIG. 8 shows both inserts installed within the container, one atop the other. The outer diameters of the sleeve portions of the inserts are only slightly smaller than the diameter of the cavity's middle section 22, thus providing a close conforming fit of the sleeves into the middle section of the cavity through the larger-diameter top section at the open top end of the container, but not so tight as to cause excessive frictional resistance to such insertion. With the insert installed and the plug engaged in the bottom wall thereof, the resulting reservoir can be filled with cleaning fluid, to a level either occupying only the lower section 20 of the cavity, or reaching up into the middle section 22 a short distance to the lower ledge and cleaning fins 30b, or even higher so long as space is left between the top surface of the liquid and the drying fins 34b at the meeting of the top and bottom ends of the cleaning fin and drying fin inserts respectively.

A cap, lid or cover 38 of the container has four circular holes 40 therein, which align with the four cavities of the container body 12 when the cap is engaged thereon. As shown in FIG. 8, at a radial distance outward from each hole 40, a respective annular rim 42 depends concentrically downward around the hole 40. The boundary wall of the hole 40 extends the full thickness of the cover 38, while the annular rim only depends downward from the only part way toward the bottom extent of the cover. An outer rim 44 depends downward from the top 46 of the cover around the full perimeter thereof, and the bottom face of this rim is coplanar with the bottom faces of the hole boundary walls to define the bottommost extent of the cover 38. An external ledge 48 around the perimeter of the container body's top end has a width closely matching the thickness of the cover's perimeter rim 44 so that the outer rim 44 sits atop the external ledge 48 to under aligned lowering of the lid onto the container body. The inner surface of the outer rim 44 conforms to the portion of container's outer wall jutting up form the ledge to the planar top of the container body, thereby providing a manually releasable friction fit of the cover on the container body. The height of this jutting portion 50 of the container's outer wall over the external ledge 48 matches the height difference between the outer rim 44 of the cover and the smaller annular rims 42 around the four holes 40. The height of the annular flange 34c of each drying fin insert 34 matches the height of the top section 18 of the respective hollow interior cavity space 16 of the container body 12, so that the annular top face of the drying fin insert 34 is coplanar with the top of the container body when the inserts are fully inserted.

Accordingly, when the cover is installed after the inserts, the annular bottom face of the rim 42 around each hole 40 abuts against the annular upper face of the respective drying fin insert 34. For each cavity, with the cleaning fin insert 30 seated atop the lower ledge 28 of the cavity wall, the drying fin insert 34 seated atop the cleaning fin insert 30 with its flange also seated atop the upper ledge 32 of the cavity wall, the annular rim 42 of the cover 38 seated atop the drying fin insert 34 and the cover 38 frictionally engaged on the container body 12, the installation of the lid thus maintains the two inserts of each cavity in their respective fixed positions therein. Accordingly, each cavity can now be used like the toothbrush cleaner container of the other embodiments. A toothbrush is passed head first into a selected cavity through the hole 40 in the cover 38 to submerge the toothbrush head into the cleaning solution in the lower section 20 of the cavity 16. The toothbrush head can then be passed back and forth through the opening between the cleaning fins 30b at the bottom of the cleaning fin insert 30 to clean out the bristles. Drawing the toothbrush further upward, the head is passed through the opening between the drying fins at the bottom of the drying fin insert, where the drying fins cause the bristles to deflect as they pass through the opening, thus drying excess cleaning liquid from the brush before it is withdrawn back out of the container through the hole in the cover 38.

The second embodiment, by having removable inserts that define the cleaning and drying fins, allows each an every fin to be easily removed from the container for cleaning or replacement. The container with multiple internal cavities also allows multiple brushes to be stored or cleaned using a single unit. For example, a family of four could make use of the illustrated embodiment by dedicating a respective cavity of the container to a respective family member, whose toothbrush, when stored in the container, provides a visual marker of whose cavity is whose.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A method of cleaning a toothbrush, the method comprising:
(a) obtaining a toothbrush cleaning apparatus comprising:
a hollow container comprising a first removable cap attached to a first upper open end, and a second removable cap or plug attached to a base of the hollow container;
the hollow container having an interior with an upper section and a lower section, the upper section being open for allowing insertion and withdrawal of the toothbrush along an axis of the container and the lower section defining a reservoir containing a cleaning liquid;
at least one cleaning fin provided on the container at a distance above a bottom of the reservoir and projecting inwardly in the interior of the container toward, without reaching, the axis; and
at least one additional fin spaced above the at least one cleaning fin and projecting inwardly in the interior of the container toward, without reaching, the axis;
(b) submerging bristles of the toothbrush in the cleaning liquid in the reservoir;
(c) with bristles on a head of the toothbrush positioned against the at least one cleaning fin, cleaning the bristles by moving the toothbrush in an upward and downward motion along the axis to position the cleaning end of the cleaning fin between the bristles as the bristles move from one side of the cleaning fin to another side thereof during passage of the head of the toothbrush along the axis; and (d) drying the bristles by pulling the bristles past a distal end of the additional fin to cause deflection of the bristles and shake off excess cleaning liquid therefrom.

2. The method of claim 1 wherein the at least one cleaning fin comprises a plurality of cleaning fins having lengths insufficient to reach the axis and leaving an opening between the cleaning fins at said axis.

3. The method of claim 1 wherein the at least one additional fin comprises a plurality of additional fins spaced above the cleaning fins.

4. The method of claim 1 comprising an additional step (e) that includes removing the at least one cleaning fin that was used in step (c) from the interior of the container.

5. The method of claim 4 wherein step (e) comprises cleaning the at least one cleaning fin that was used in step (c) after removal thereof from the interior of the container, and placing the at least one cleaning fin used in step (c) back into the interior of the container for re-use.

6. The method of claim 4 comprising replacing the at least one cleaning fin that was used in step (c) with at least one new cleaning fin.

7. The method of claim 4 comprising at least one repetition of steps (c) and (d) before performing step (e).

\* \* \* \* \*